(12) United States Patent
Andersson

(10) Patent No.: US 10,569,008 B2
(45) Date of Patent: *Feb. 25, 2020

(54) MOTORIZED IRRIGATION SYSTEM

(71) Applicant: DENTSPLY IH AB, Mölndal (SE)

(72) Inventor: Fredrik Andersson, Göteborg (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/978,724

(22) Filed: May 14, 2018

(65) Prior Publication Data

US 2018/0256808 A1 Sep. 13, 2018

Related U.S. Application Data

(63) Continuation of application No. 13/929,213, filed on Jun. 27, 2013, now Pat. No. 9,968,728.

(Continued)

(30) Foreign Application Priority Data

Jun. 29, 2012 (EP) .................................. 12174484
Dec. 21, 2012 (EP) .................................. 12199180

(51) Int. Cl.
*A61M 3/02* (2006.01)

(52) U.S. Cl.
CPC ............ *A61M 3/0258* (2013.01); *A61M 3/02* (2013.01); *A61M 3/0262* (2013.01); *A61M 3/0295* (2013.01); *A61M 3/0237* (2013.01); *A61M 3/0254* (2013.01); *A61M 2205/35* (2013.01); *A61M 2205/3553* (2013.01);

(Continued)

(58) Field of Classification Search
CPC .... A61M 3/02; A61M 3/0225; A61M 3/0233; A61M 3/025; A61M 3/0254; A61M 3/0258

See application file for complete search history.

(56) References Cited

U.S. PATENT DOCUMENTS 3,731,676 A    5/1973   Rebold
5,944,684 A    8/1999   Roberts et al.
(Continued)

FOREIGN PATENT DOCUMENTS

CN    1259879    7/2000
CN    2496467    6/2002
(Continued)

OTHER PUBLICATIONS

Chinese Office Action issued for Chinese Patent Application No. 2013800290949, dated Apr. 8, 2018 (9 pages).

(Continued)

*Primary Examiner* — Laura A Bouchelle
(74) *Attorney, Agent, or Firm* — Perkins Coie LLP

(57) ABSTRACT

A portable irrigation system includes a reservoir for an irrigation liquid, a probe for arrangement in a user, an electrical system that directly or indirectly pumps the irrigation liquid from the reservoir to the probe, a control unit coupled to the electrical pump to control the electrical pump and to transfer the irrigation liquid, and tubing to provide fluid communication between the reservoir, the control unit and the probe. The control unit also includes at least one manually operable control element to control the electrical pump.

23 Claims, 9 Drawing Sheets

Related U.S. Application Data

(60) Provisional application No. 61/667,597, filed on Jul. 3, 2012.

(52) U.S. Cl.
CPC . *A61M 2205/3576* (2013.01); *A61M 2205/50* (2013.01); *A61M 2205/58* (2013.01); *A61M 2210/1064* (2013.01); *A61M 2210/1067* (2013.01)

(56) References Cited

U.S. PATENT DOCUMENTS

| | | | |
|---|---|---|---|
| 6,106,506 | A | 8/2000 | Abell et al. |
| 6,228,048 | B1 | 5/2001 | Robbins |
| 6,485,451 | B1 | 11/2002 | Roberts et al. |
| 6,503,220 | B1 | 1/2003 | Cirillo et al. |
| 6,689,091 | B2 | 2/2004 | Bui et al. |
| 6,768,425 | B2 | 7/2004 | Flaherty et al. |
| 6,984,226 | B1 | 1/2006 | Abell et al. |
| 7,000,267 | B2 | 2/2006 | Chesters |
| 7,294,120 | B1 | 11/2007 | Eidsen et al. |
| 8,545,440 | B2 | 10/2013 | Patrick et al. |
| 9,919,093 | B2 | 3/2018 | Andreen et al. |
| 9,968,728 | B2 * | 5/2018 | Andersson .......... A61M 3/0258 |
| 2003/0073963 | A1 | 4/2003 | Falconer |
| 2006/0009732 | A1 | 1/2006 | Hardy |
| 2006/0150310 | A1 | 7/2006 | Tsai |
| 2006/0178632 | A1 * | 8/2006 | Trombley, III ....... A61M 5/007 604/151 |
| 2006/0264831 | A1 | 11/2006 | Skwarek et al. |
| 2007/0073216 | A1 | 3/2007 | McAuliffe et al. |
| 2007/0118015 | A1 | 5/2007 | Wendlandt |
| 2009/0143734 | A1 * | 6/2009 | Humayun .......... A61F 9/00736 604/151 |
| 2010/0063436 | A1 * | 3/2010 | Tanghoej ............ A61M 3/0254 604/28 |
| 2010/0076372 | A1 | 3/2010 | Hacker et al. |
| 2010/0268154 | A1 | 10/2010 | Vining |
| 2011/0021905 | A1 | 1/2011 | Patrick et al. |
| 2011/0224600 | A1 | 6/2011 | Orlandi |
| 2011/0282251 | A1 | 11/2011 | Baker et al. |
| 2012/0078170 | A1 | 3/2012 | Smith et al. |
| 2012/0143168 | A1 | 6/2012 | Bjerregaard |
| 2014/0005602 | A1 | 1/2014 | Andreen et al. |
| 2014/0155864 | A1 | 6/2014 | Andreen |
| 2016/0193403 | A1 | 7/2016 | Andersson |

FOREIGN PATENT DOCUMENTS

| | | | |
|---|---|---|---|
| CN | 2624928 | | 7/2004 |
| CN | 2746917 | | 12/2005 |
| CN | 101583385 | | 11/2009 |
| CN | 102302810 | | 1/2012 |
| CN | 101912640 | | 1/2013 |
| CN | 102481402 | | 1/2015 |
| EP | 582032 | | 2/1994 |
| EP | 1946786 | | 7/2008 |
| EP | 1946786 | A1 * | 7/2008 .......... A61M 3/0254 |
| GB | 238038 | | 8/1925 |
| RU | 2014090 | | 6/1994 |
| RU | 2306154 | | 9/2007 |
| RU | 2452522 | | 6/2012 |
| WO | 2003030968 | | 4/2003 |
| WO | 2003030969 | | 4/2003 |
| WO | 2008087220 | | 7/2008 |
| WO | 2008087221 | | 7/2008 |
| WO | 2009092380 | | 7/2009 |
| WO | 2011023196 | | 3/2011 |
| WO | 2013076446 | | 5/2013 |
| WO | 20130160380 | | 10/2013 |

OTHER PUBLICATIONS

Russian Office Action issued for Russian Patent Application No. 2014146512, dated Mar. 13, 2017, with translation (15 pages).
Russian Office Action issued for Russian Patent Application No. 2014146511, dated Mar. 13, 2017, with translation (15 pages).
Russian Office Action issued for Russian Patent Application No. 2014146515, dated Mar. 13, 2017, with translation (13 pages).
European Office Action issued for European Patent Application No. 13167020.0, dated Oct. 22, 2015 (4 pages).
Chinese Office Action issued for Chinese Patent Application No. 2013800290760, dated Apr. 22, 2016 (16 pages).
Chinese Office Action issued for Chinese Patent Application No. 2013800290949, dated Jan. 12, 2016 (15 pages).
Final Office Action issued for U.S. Appl. No. 13/929,312, dated Apr. 25, 2017 (18 pages).
European Search Report, Application No. 12199180.6, Published Jun. 21, 2013.
European Search Report, Application No. 13167020.0, Published Sep. 5, 2013.
International Search Report and Written Opinion, Application No. 2013/063212, Published Jun. 25, 2013.
International Search Report and Written Opinion, Application No. 2013/063242, Published Jun. 25, 2013.
International Search Report and Written Opinion, Application No. 2013/063256, Published Jun. 25, 2016.

* cited by examiner

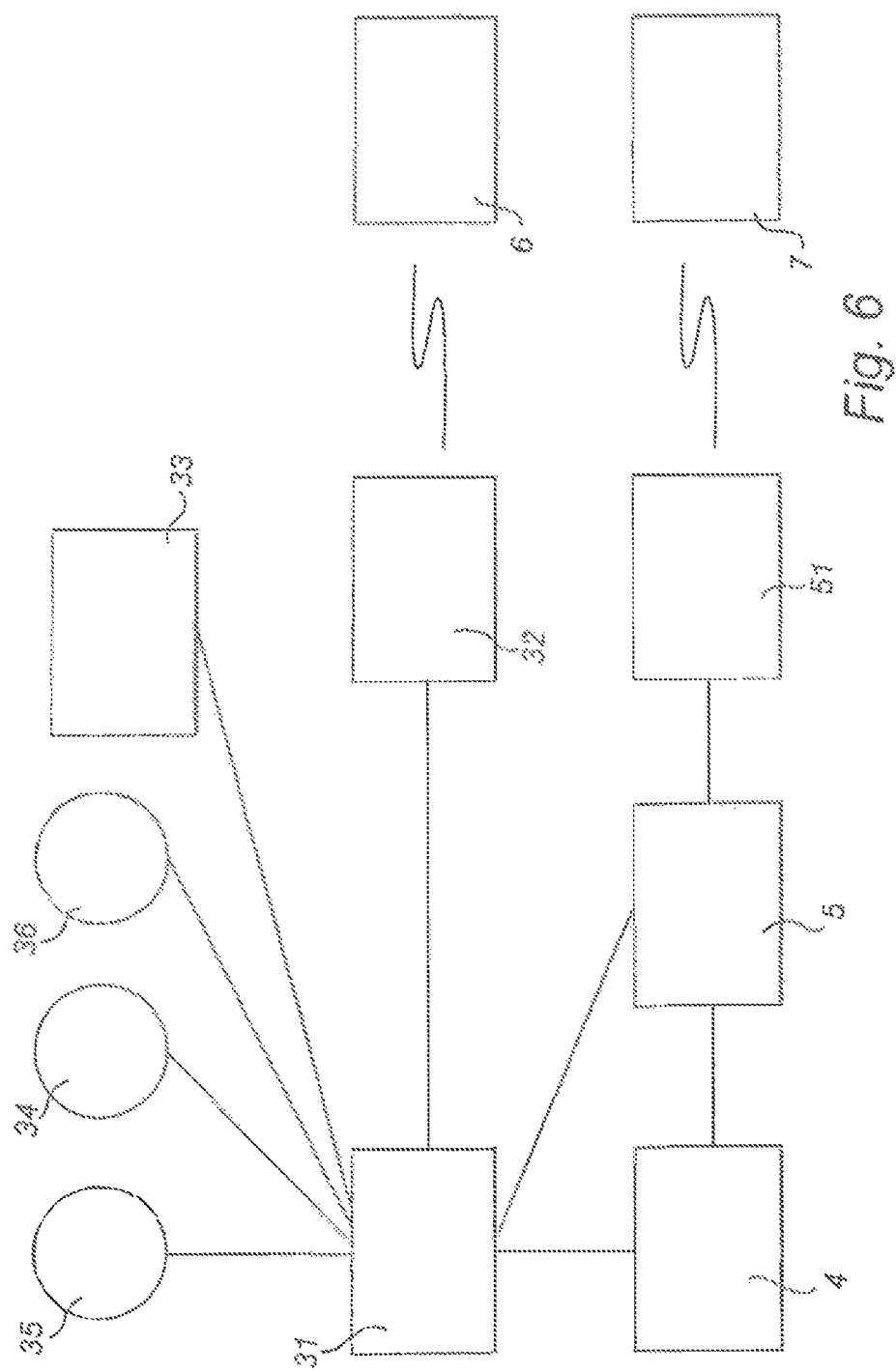

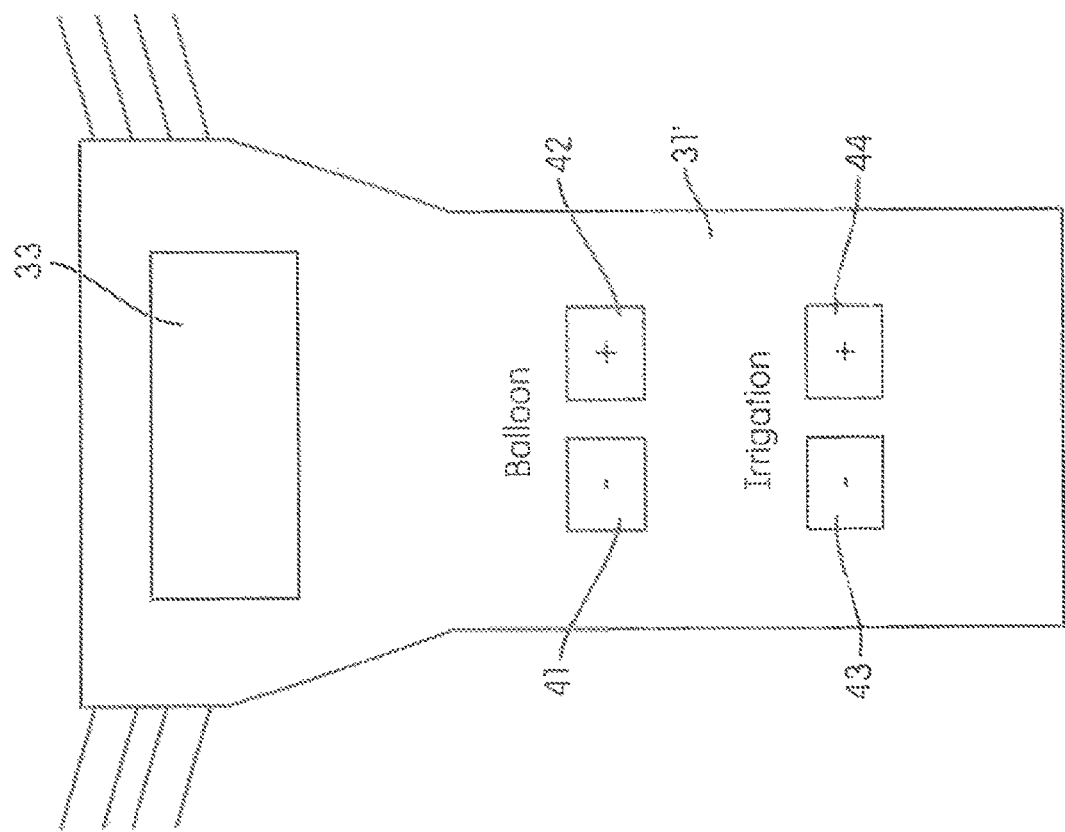

MOTORIZED IRRIGATION SYSTEM

CROSS-REFERENCE TO RELATED APPLICATIONS

This patent application is a continuation of U.S. patent application Ser. No. 13/929,213, filed Jun. 27, 2013, which further claims the benefit of and priority to European Application Ser No. 12174484.1, filed on Jun. 29, 2012, European Application Ser No. 12199180.6, filed on Dec. 21, 2012, and U.S. Provisional Patent Application Ser. No. 61/667,597, filed on Jul. 3, 2012, which are herein incorporated by reference for all purposes.

FIELD OF THE INVENTION

The present invention relates to an irrigation system, comprising a reservoir for an irrigation liquid, a probe for arrangement in a user, and a control unit. The irrigation system is particularly intended for rectal irrigation, and is suitable for self-administration of an irrigation liquid.

BACKGROUND OF THE INVENTION

The present invention relates to an irrigation device. Administrating an irrigation liquid is a common medical procedure whereby liquid is injected into a bodily cavity, such as into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation. To this end, irrigation systems may be used e.g. by people suffering from spinal cord injuries, spina bifida or multiple sclerosis. For such users, irrigation may improve quality of life by preventing constipation, reducing time spent for bowel emptying procedures, reducing fecal incontinence, and by increasing independency in general.

Irrigation is nowadays often performed outside medical attendance premises, such as in the patient's home, and is also often performed by the patient himself, i.e. by self-administration. Hereby, the patient need to do multiple tasks at the same time, or immediately following on each other, such as inserting the probe in a correct position, adequately fixating the probe in the bodily cavity, enabling the liquid to be discharged for irrigation and discharge a correct dose of irrigation liquid, and removing the probe after use. Further, many of the users of irrigation systems have reduced dexterity, which makes the operation even more cumbersome.

It is further of importance that the irrigation system is of a limited size, and portable. Portability of the irrigation system is important to disabled persons who are not hospitalised or bed-ridden if they are to live as normal a life as possible. This is particularly important if they travel away from their home, for instance, to someone else's home or if they stay in a hotel. In this situation, they need to be able to deal with their bowel function easily.

Various irrigation systems are known in the art, such as is disclosed in WO 2008/087220, WO 2009/092380, WO 03/030969, WO 2011/023196 and WO 03/030968. However, despite the attempts to make these devices user friendly, all of these irrigation devices are still relatively complicated to use, especially for self-administration of the irrigation liquid, and also, most of these known devices are made of many different components and are relatively costly to produce.

It is also known to use electrical pumps in irrigation systems. For example, such irrigation systems are disclosed in WO 08/087221 and EP 0 582 032. However, these systems are also subject to various problems, such as being large, complex and expensive. Further, the electrical systems of these known systems are also sensitive, and are easily deteriorated or destroyed by the environment in which they are used, were water is often spilled, etc. It may also be difficult to ensure that the irrigation system is always operated in a safe way, and unintended use of the system, either on purpose or by accident, may lead to discomfort or even hazard to the user/patient.

There is therefore a need for an irrigation device which can be used safely, easily and conveniently for self-administration of the irrigation liquid, and which can be produced in a cost-efficient way.

SUMMARY OF THE INVENTION

In view of the above mentioned need, a general object of the present invention is to provide an irrigation system which alleviates the above-discussed problems of the prior art, and at least partly fulfils the above-discussed needs.

This and other objects are achieved with an irrigation system according to the appended claims.

According to a first aspect of the invention, there is provided a portable irrigation system comprising:
  a reservoir for an irrigating liquid;
  a probe for arrangement in a user;
  an electrical system, comprising:
    an electrical pump for directly or indirectly pumping irrigation liquid from the reservoir to the probe;
    a control unit for controlling the electrical pump, and thereby also the transfer of said irrigation liquid; and
    tubing providing fluid communication between said reservoir, control unit and probe;
    wherein said control unit comprises at least one manually operable control element, such as a control button, for controlling said electrical pump, said control element being switchable between an activated state, in which the electrical pump is controlled to pump irrigation liquid, and a deactivated state, in which the electrical pump is controlled not to pump irrigation liquid, and wherein the control element is brought into the activated state by continuous application of a predetermined condition thereto, and wherein the control element is immediately brought to the deactivated state when the predetermined condition ceases to be applied, thereby aborting pumping of the irrigation liquid.

According to another aspect of the invention, there is provided a portable irrigation system comprising:
  a reservoir for an irrigating liquid;
  a probe for arrangement in a user;
  an electrical system, comprising:
    an electrical pump for directly or indirectly pumping irrigation liquid from the reservoir to the probe;
    a control unit for controlling the electrical pump, and thereby also the transfer of said irrigation liquid; and
    tubing providing fluid communication between said reservoir, control unit and probe;
    wherein said control unit comprises at least one manually operable control element, such as a control button, for controlling said electrical pump, said control element functioning as a dead man's handle, thereby immediately returning to a deactivated state, in which the electrical pump is controlled not to pump irrigation liquid, when manual operation of the control element is aborted.

An electric pump is of great advantage in irrigation systems of this type, since it can be operated very easily, which is particularly advantageous for users with reduced dexterity. If the user lacks strength in their hands it may be easier for them to operate an electric pump rather than squeezing e.g. a foil-pump. The electric pump can also easily be adjusted and customized for different types of use, for different types of users, etc. However, a drawback with electric pumps is the risk of pumping too long or at too high speed, or the like, which may lead to discomfort and even hazard to the user. By means of the present invention a so-called dead man's handle functionality is obtained, meaning that pumping is immediately aborted when the control element is released. This means that the pumping action is stopped immediately when the control element is released, regardless of whether this release is intentional or by accident. For example, the pumping will stop immediately if the control element is accidentally dropped. Further, stopping by releasing is a very intuitive and quick operation method, which is both ergonomically favourable and fast.

The predetermined condition to bring the control element into the activated state is preferably at least one of depression, twisting, rotating, pulling and pushing. If a control button is used, the predetermined condition is preferably depression, so that the control button is activated by depressing it, and deactivated by releasing it. However, alternative types of control elements, such as rotatable knobs, switching levers and the like may also be used. The automatic return to the deactivated state when the predetermined condition ceases can e.g. be obtained by a spring, an elastic element, or the like, operable to provide a counterforce to the force applied by the manual operation.

The control unit may be connected to the rest of the irrigation system by means of wire, and thereby be physically connected to the electric pump. Alternatively, the control unit may be a remote control, which is wirelessly connected to the rest of the irrigation system. The remote control can e.g. be at least one of: a smart phone, a tablet computer and a laptop computer. It is also possible to combine an integrated control unit and a remote control, whereby the user may chose whether to use the integrated control unit or the remote control, or both, for controlling the irrigation process.

According to one embodiment, the electrical system further comprises:
- a battery for driving the electrical pump,
- at least one control switch for activation of the electrical pump, and
- wiring connecting said parts to each other; wherein said control unit comprises a waterproof housing enclosing at least said battery and wherein, the electrical system is galvanically isolated from the exterior of the irrigation system, and wherein said battery is chargeable through inductive charging.

The waterproof housing and the galvanic separation between the electric system and the surrounding environment makes the system very robust. It can hereby withstand for example spilling of water, or even accidental submersion of the control unit etc. in water. Since an irrigation system is typically used in close relation to water and other liquids, this an important advantage. This also makes it possible to use the system, or components of the system, for longer time, which provides a better overall cost-efficiency.

Preferably, the entire electrical system is enclosed within the waterproof control unit. However, parts of the electric system may extend outside the control unit, e.g. when a submersible pump is to be used, as long as the electric system is still galvanically separated from the exterior. In some embodiments, it is even possible to arranged most of the electrical system outside the control unit, e.g. in a separate housing.

Preferably, all components of the system are individually exchangeable, so that e.g. the catheter can be exchanged frequently, and typically be used only once, whereas other parts of the system, such as the control unit, the electrical system and the irrigation liquid reservoir can be used for months or even years.

Further, since the battery is inductively chargeable, no electrical connections are needed for charging. Thus, the electrical system does not need any open electrical connections, thereby providing a complete galvanic separation from the environment.

The irrigation system of the present invention comprises relatively few and uncomplicated components, and which may be reused for a long time, which makes the irrigation system relatively easy and cost-efficient to produce. Further, the irrigation system lends itself well for automated or semi-automated manufacturing.

As discussed above, the dead man's handle functionality makes the system easy and safe to use, in particular for persons with reduced dexterity. Further, the provision of the galvanically isolated electrical system, the irrigation system is safe and easy to use, also for persons with reduced dexterity. This also makes the irrigation system highly suitable for self-administration of the irrigation liquid. The control element(s) on the control unit makes it easy to access the pump with one hand only, and to switch between different pumping modes etc. Typically with this arrangement, it is e.g. possible to operate the irrigation system with one finger, e.g. the thumb. This provides a very convenient and precise controllability of the irrigation system.

Inductive charging uses an electromagnetic field to transfer energy from a charging station to the battery to be charged. Energy is sent through an inductive coupling to a receiving circuit within the control unit, which then uses the received energy to charge the battery. For charging, the control unit may be placed on or close to a charging station.

Preferably, the control unit further comprises at least one control element, such as a control button, arranged on the surface of the housing for operating the control switch(es). The control elements may be realized as a areas on a touch screen.

However, alternatively or additionally, the control element(s) may be arranged on a separate control, connected e.g. by an isolated wire to the control unit. Hereby, the control can be made small, and easy to use and handle. The control may also be wirelessly connected to the control unit, and thereby function as a wireless remote control. For example, a smart phone, tablet computer, laptop computer or the like may comprise an application/software which makes it useable as a remote control for the irrigation system.

The electric pump may be arranged to pump irrigation liquid from the reservoir to the probe directly or indirectly. By direct pumping is here meant that the pumping is made directly on the irrigation fluid. Such a pump may e.g. be arranged in-line in a conduit leading from the reservoir to the probe. By indirect pumping is here meant that the pumping is made on a different fluid, such as air, which when pumped exerts a pressure to the irrigation fluid, whereby the irrigation fluid is also pumped. For example, the first pump may be arranged to pump a gas, and preferably air, into the reservoir to create a pressure in the reservoir to displace the irrigation liquid therefrom and feed it to the probe.

According to one embodiment, the electrical pump is a submersible pump, and arranged within the reservoir. To operate this pump, isolated electric wiring is preferably arranged between the pump and the battery in the control unit. Alternatively, the pump may be arranged along the tubing connecting the reservoir and the probe. In this alternative solution, the electric pump is preferably arranged within the waterproof housing of the control unit.

Further, the pump may be a peristaltic pump where the liquid or air is moved along the tube by applying pressure to the outside of the tube. Such a pump comprises impellers placed around an axle, which may be turned by an electric motor. A peristaltic pump would preferably be used to suck the liquid from the reservoir and pump it into the rectum.

It is further preferred that the control unit is arranged at a distance from both the reservoir and the probe, and being connected to the reservoir and probe, respectively, through the tubing. This makes it possible to have the reservoir at a distance from the control unit, e.g. on the floor, and still provide a good working position for the user.

The control unit is preferably programmable. For example, the control unit may be programmable to set at least one of: total irrigation liquid volume to be discharged and irrigation liquid discharge flow rate. The pump may be pre-programmed with a number of programmes or it may be programmed via the control element(s) or through an external remote control or the like. The pump may be programmable so as to automatically carry out a predefined program. A user that frequently uses anal irrigation may experience a preferred way of carrying out the irrigation process. Then it is of advantage to be able to programme this way into the pump system, so that the irrigation process is done the most preferred way every time. Furthermore, caregivers may have a certain experience concerning the optimum process, which they can programme into the pump system. Thereby errors will be reduced.

The control unit preferably comprises at least two control elements, such as control buttons, and preferably at least three control elements. Two, or preferably three, control elements enables a very easy manipulation of the control unit, and at the same time provides numerous input alternatives. It is further preferred that at least one of the control element(s) is a multi-purpose control element having different functions in different operation states. Hereby, the control elements can e.g. be assigned to control different functions during initiation/set-up, during filling of the reservoir and priming of the system, during insertion and fastening of the probe in the operative position, during irrigation, during withdrawal of the probe, and/or after completed irrigation.

For inflation of the balloon, any fluid may be used. For example, it is possible to connect the pump to the reservoir, and use irrigation liquid for filling of the balloon. It is also possible to provide a separate supply of another fluid, liquid or gas, for filling of the balloon. However, preferably ambient air is used for inflation of the balloon.

In one embodiment, the electrical pump may be useable both for pumping irrigation liquid for discharge through the probe and for pumping a fluid for filling of an inflatable retention member on the probe. If the electrical pump is arranged to pump air or any other gas to the reservoir, for indirect pumping of the irrigation fluid, the electrical pump may also be arranged to pump air or any other gas to the retention member. The pump may also be of a type capable of pumping different fluids, such as a membrane pump, which can pump one fluid, e.g. irrigation liquid, on one side of the membrane, and another fluid, e.g. air, on the other side of the membrane.

Alternatively, a second pump may be arranged to pump air or liquid, such as irrigation liquid, to the retention member. The second pump may also be an electric pump, arranged within the electric system of the irrigation system. However, the second pump may also be a manually pump, such as a bulb or a bellow pump. The manually operable pump may be a bulb pump, comprising an inlet provided with a one-way valve, allowing a fluid to enter but not exit the pump, a pumping compartment and an outlet, provided with a one-way valve, allowing a fluid to exit but not enter the pump. The pumping compartment is made of a resilient, squeezable material, which retains it shape when unloaded. By squeezing the pumping compartment, the fluid is pumped out through the outlet, and when the squeezing is relieved, the pumping compartment retains its original shape, thereby sucking in fluid through the inlet.

A manually operable pump is very cost-efficient, which lowers the overall costs of the product. Further, a manually operable pump provides a very precise controllability for the user, which is useful for the very limited fluid volume needed for adequate inflation of the retention member/balloon, and considering the importance of the balloon being inflated with precision. Too low inflation may result in a too weak fixation, which may result in the probe falling out during irrigation. Too high inflation may be painful and even potentially harmful to the user. However, similar precise control may be achieved by means of an electric pump, which may be arranged to pump at low flow rates and with very precise control.

One or several valves may also be arranged to release fluid from the retention member, and/or to release overpressure from the reservoir. When air is used as a filling fluid for the retention member/balloon, the valve for releasing fluid from the balloon may open up to a vent channel. The valve is in this embodiment closed by default, and opened up whenever the balloon filling fluid is to be released. If e.g. irrigation liquid is used, the valve may instead release the irrigation liquid back to the reservoir or into the probe for discharge during irrigation. However, it is also possible to release the fluid from the balloon into a drain compartment or the like.

In a preferred embodiment, the control unit comprises a valve for releasing fluid from the retention member for deflation, said valve being controllable by a control element, and preferably a control button.

The control unit may also, as discussed above, be remotely controllable by a remote control arranged to communicate with the control unit via wireless communication. Hereby, the control unit may e.g. be placed on the floor, or in any other resting position, and instead be operated through the remote control during irrigation. This facilitates handling of the irrigation system, and affords the user an increased freedom in terms of how to use the system. The remote control may be a dedicated remote control, specifically arranged to control the irrigation system. However, the remote control may also be a common wireless device, capable of transmitting wireless control signals to a receiver in the control unit. In one preferred embodiment, the remote control is a mobile telephone, and preferably a smart phone. Additionally or alternatively, the remote control may be a laptop computer or a tablet computer. Hereby, a special application may be downloaded to the smart phone/laptop/ tablet computer, providing a suitable interface for the device, and enabling it to send appropriate control signals to the control unit.

The wireless communication between the control unit and a remote control or a remote unit may be obtained in many ways, as is per se well known in the art, such as by infrared light (IR), ultrasonic communication, radio frequency (RF) communication, such as Bluetooth, etc.

The control unit may further be arranged to transmit operation related data to a remote unit via wireless communication. For example, such data may be sent to a smart phone or the like. Hereby, the irrigation procedures may e.g. be logged over time, to facilitate follow-ups and also enabling a more adequate setting of parameters for forthcoming irrigations.

The control unit further preferably comprises a display. The display may be used to display information to the user about the progress of the irrigation procedure, such as volume that has been pumped, present flow rate, time elapsed from the start of the procedure, or estimated time left, etc. Further, the display may be used to guide the user about what choices in terms of settings and the like that are needed, the present function of the control elements, etc. Still further, the display may be a touch screen, useable also for inputting data into the system. For example, the control elements may be realized as areas on the touch screen. If the control unit is connected wirelessly to a remote control or other remote unit, the display on this device may be used to display information as well. Thus a display on a remote control or other remote unit may be used to replace the display on the control unit, or to complement a display on the control unit.

According to another aspect of the present invention, there is provided a use of the irrigation device as discussed above for rectal irrigation.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 6 is a schematic block diagram of an irrigation system according to still another embodiment of the present invention;

FIG. 8 is a schematic overview of an alternative embodiment of a control unit useable in irrigation systems of the present invention.

DESCRIPTION OF PREFERRED EMBODIMENTS

Figure 1:
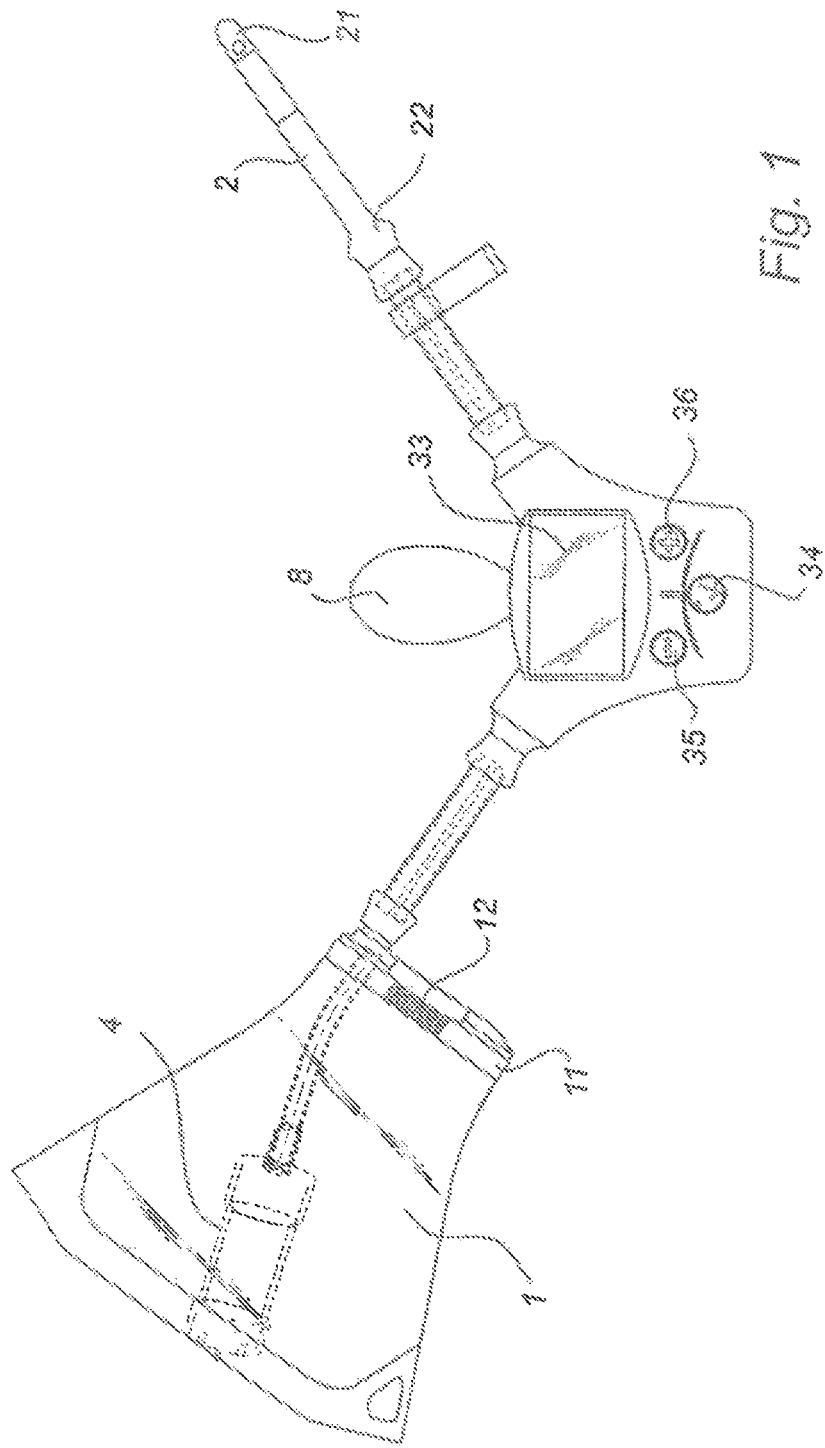
FIG. 1 is schematic overview of an irrigation system according to a first embodiment of the invention.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

FIG. 1 discloses an irrigation system according to a first exemplary embodiment, comprising a reservoir 1 for an irrigating liquid, a probe 2 for arrangement in a user, and a control unit 3.

The reservoir may be realized in various ways. For example, the reservoir may be formed by a rigid, semi-rigid or flexible material. In case a semi-rigid or flexible material is used, the reservoir may be collapsible or foldable, to make the irrigation system more compact prior to use. The reservoir is provided with an opening, closed by a lid 11, for filling of the reservoir. Tubing connecting the reservoir to the rest of the irrigation system may be provided through the lid 11, or through other access points on the reservoir.

In order to render the irrigation system as portable as possible, the container preferably has a capacity of less than 5 litres, more preferred less than 3 litres and most preferred less than 2 litres. If however the system is to be used for repeated irrigation, a larger capacity container may be necessary.

The reservoir may comprise an overpressure release valve, to release pressure over a predetermined maximum pressure to be allowed. Further, the reservoir preferably comprises a filter 12, such as a hydrophobic filter, which is impermeable to the irrigation liquid, but which allows air to enter the reservoir but not escape the reservoir. Such a filter ensures that the reservoir maintains its shape when irrigation liquid is being pumped out from the reservoir. This is of advantage, since it makes the reservoir more stable. It also makes it possible to use less costly materials and less rigid containers when producing the reservoir, thereby making the production more cost-efficient. This ensures that the reservoir remains stable during irrigation. However, alternative means for obtaining this are also feasible. For example, the reservoir may simply be provided with an air inlet, possibly provided with a back-valve to prevent outflow of irrigation liquid, should the irrigation liquid reach the inlet. Alternatively, the electric pump may be arranged both to pump liquid out from the reservoir, and simultaneously pump a corresponding volume of air into the reservoir.

The probe 2 is provided with a retention member, such as an inflatable balloon 21, for fixing the catheter in a body cavity. Further, the probe may be provided with a rearward enlarged part 22, providing an abutment to hinder too deep insertion. The probe is provided with two lumens—one lumen for transfer of irrigation liquid through the probe, for discharge at the forward end, and one lumen for inflation and deflation of the balloon.

An electric pump 4 for pumping irrigation liquid is here provided as a submersible pump, arranged in the reservoir. The pump is part of the electrical system of the irrigation system, connecting the pump inter alia to to a battery. The electrical system is disclosed in further detail with reference to FIG. 5A and FIG. 5B in the following.

The control unit is here realized as a unitary, hand-held unit. The control unit comprises a display 33, and three control elements 34, 35 and 36. The control element is preferably realized as a depressible control button. The control unit is waterproof. The control elements may thus be realized with thick pliable plastic or the like, designed to withstand many pushes. The further details and function of the control unit will be discussed in more detail in the following.

In this embodiment, a second pump 8 is arranged to pump fluid into the balloon of the probe. The pump is a manually operable pump. However, other types of pumps are also feasible. In the shown example, the manually operable pump is a bulb pump, comprising an inlet, provided with a one-way valve, allowing a fluid to enter but not exit the pump. Further, the pump comprises a pumping compartment and outlets, provided with a one-way valve, allowing a fluid to exit but not enter the pump. The pumping compartment is made of a resilient, squeezable material, which retains it shape when unloaded. By squeezing the pumping compartment, the fluid is pumped out through the outlet, and when the squeezing is relieved, the pumping compartment retains its original shape, thereby sucking in fluid through the inlet. In the illustrative example, the pump is used to pump air. Thus, the second pump 8 pumps air into the balloon 21 for inflation. The air is releasable through a valve (not shown).

Tubing is arranged to connect the reservoir, control unit and probe together. Preferred materials for the bulb pumps and the balloon can be any suitable material e.g. such as PVC, latex, TPE or PU. However, other materials providing similar properties can likewise be used.

Figure 2:
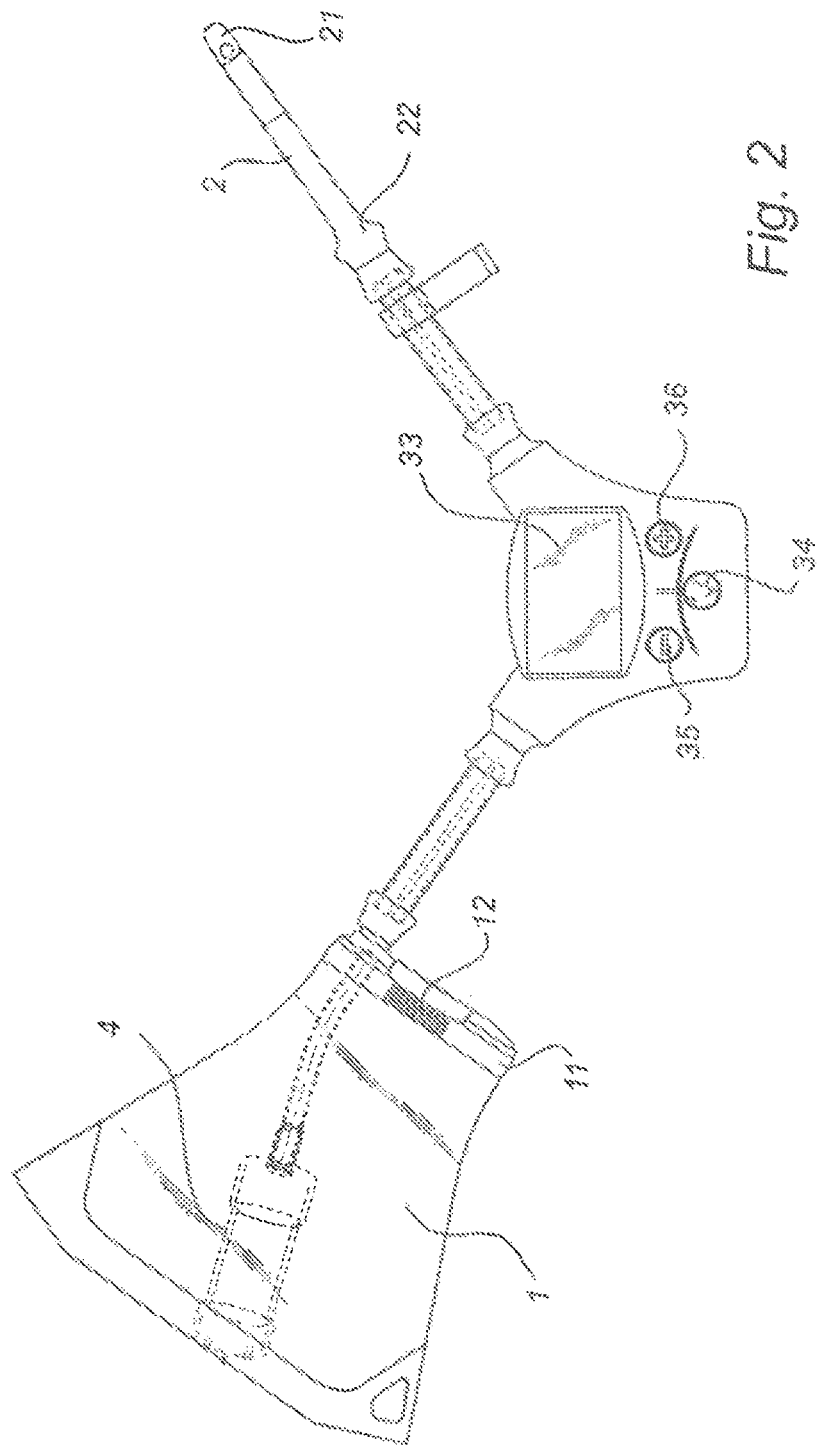
FIG. 2 is a schematic overview of an irrigation system according to a second embodiment of the invention.

The second embodiment, illustrated in FIG. 2, resembles the above-described first embodiment. However, here the electrical pump 4 is also useable to inflate the balloon 21 of the probe. Consequently, there is no need for the second pump 8.

Figure 3:
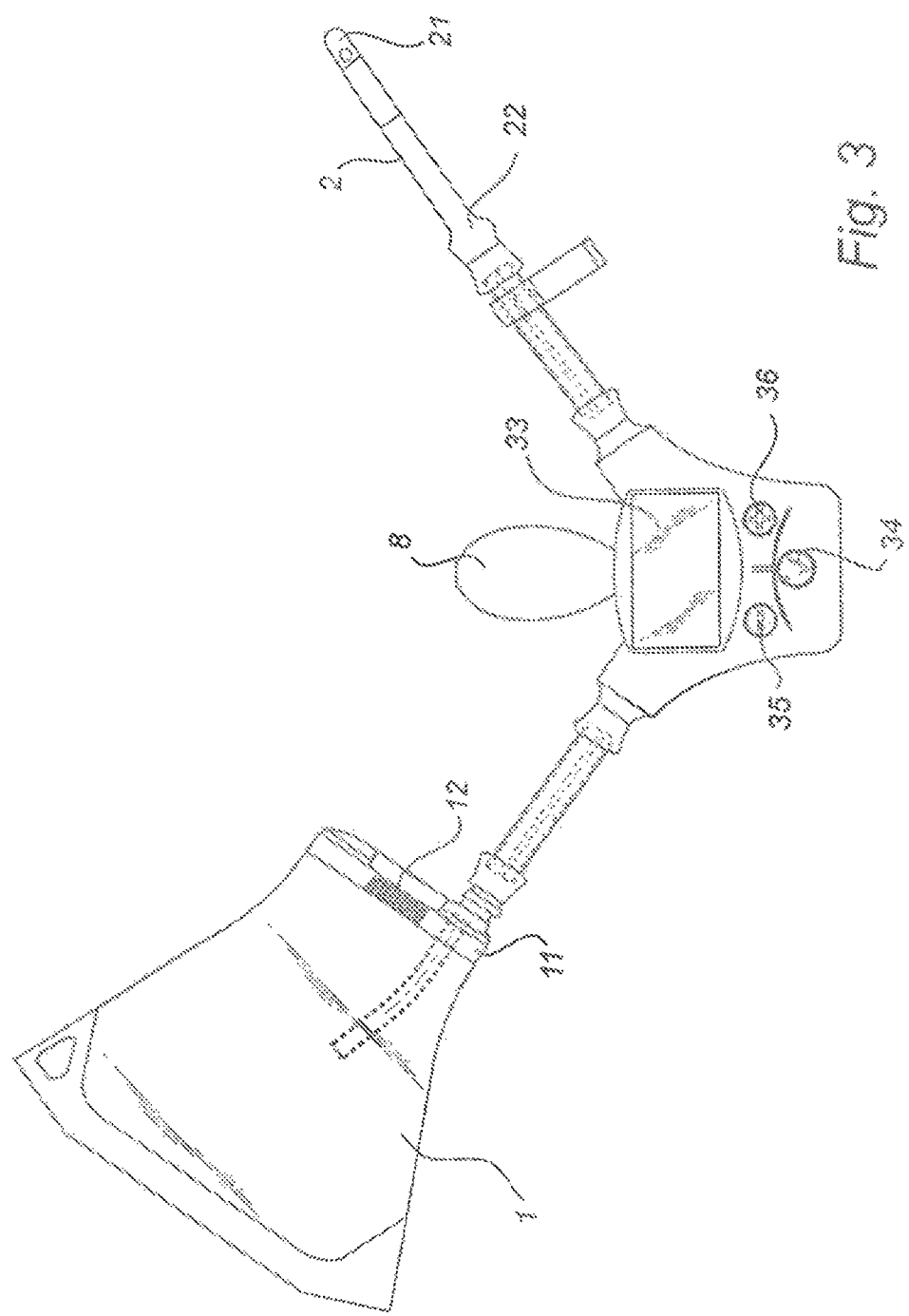
FIG. 3 is schematic overview of an irrigation system according to a third embodiment of the invention.

The third embodiment, illustrated in FIG. 3, also resembles the above-described first and second embodiments. However, here the electrical pump 4 is arranged within the control unit 3. As in the embodiment of FIG. 1, a separate second pump 8, here a hand-operated bulb pump, is arranged to inflated the balloon.

Figure 4:
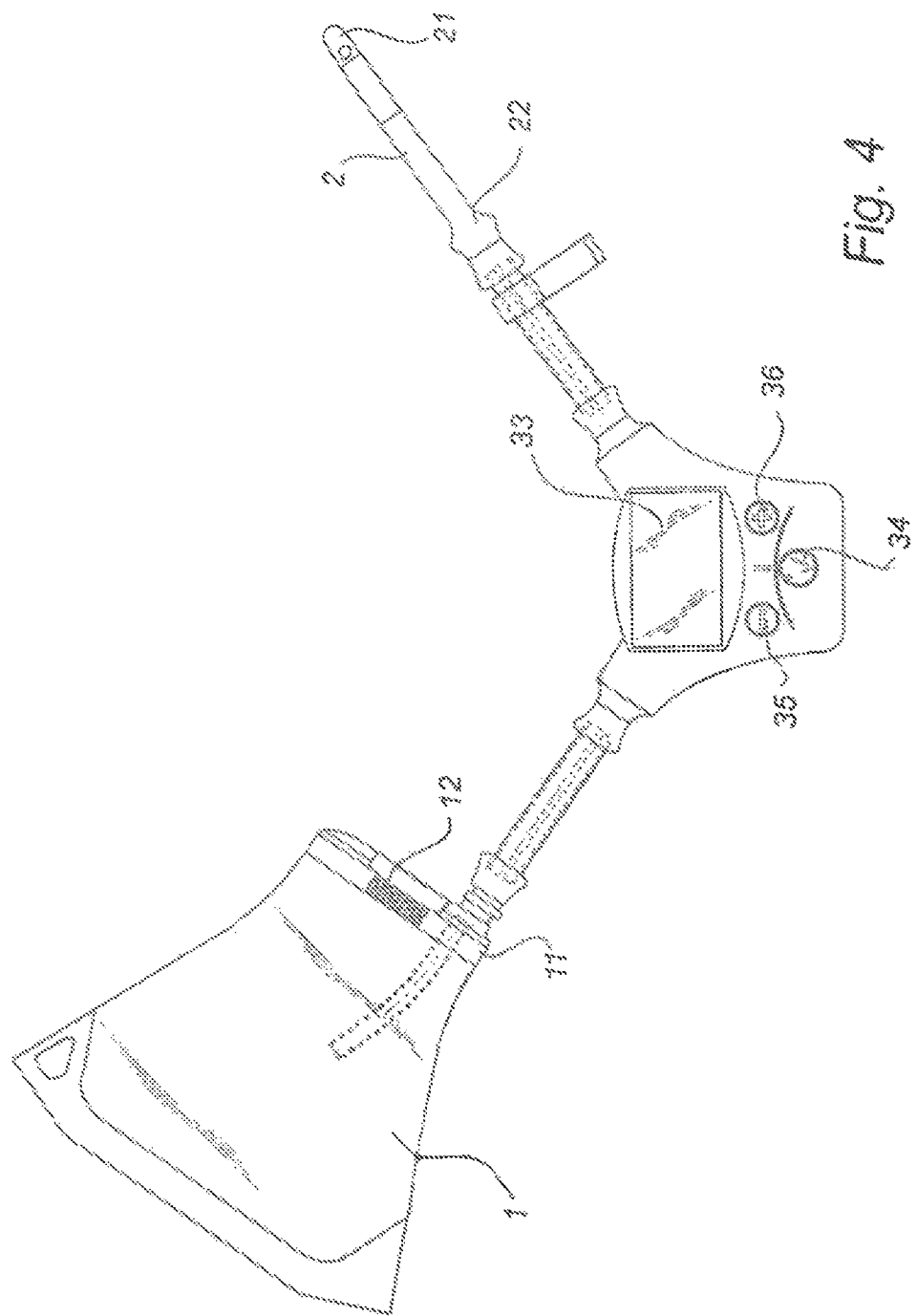
FIG. 4 is a schematic overview of an irrigation system according to a fourth embodiment of the invention.

The fourth embodiment, illustrated in FIG. 4, resembles the above-described embodiments. Here, the electrical pump 4 is arranged within the control unit 3, as in the third embodiment, and the electric pump is also useable to inflate the balloon 21 of the probe, as in the second embodiment.

The electrical system of the irrigation system will now be discussed in more detail, with reference to FIG. 6. The electrical system comprises an electric pump 4, as previously disclosed, connected to a battery 5 and a controller 31, such as a micro-processor. The controller 31 is further connected to the display 33, and to switches activated by means of the control elements 34-36. Further, the controller is optionally connected to a wireless transceiver 32, which is adapted to transmit and receive data from a remote unit 6. Hereby, the remote unit may provide control data to the controller 31, for remote control of the control unit. Additionally or alternatively, the controller may transmit data about the irrigation procedure to the remote unit. The remote unit 6 may e.g. be a remote control, a smart phone or the like. The battery 5 is further connected to a charging circuit 51, adapted to receive inductive charging from a charging station 7. All elements of the electrical system are connected by electrical wires. Further, the electrical system is preferably galvanically isolated from the rest of the irrigation system and the environment.

At least the control element used to operate the electric pump is provided with a dead man's handle functionality. Thus, the control element is brought into the activated state by continuous application of a predetermined condition thereto, and is immediately brought to the deactivated state when the predetermined condition ceases to be applied, thereby aborting pumping of the irrigation liquid. In addition, some or all of the other control elements may also be provided with dead man's handle functionality. The automatic return to the deactivated state when the predetermined condition ceases can e.g. be obtained by a spring, an elastic element, or the like, operable to provide a counterforce to the force applied by the manual operation.

The irrigation liquid can be any liquid which is capable of irrigation the body cavity of interest. In order to stimulate bowel movements suitable irrigation liquids includes water, hypertonic aqueous salt solutions, solutions or suspensions of cathartic agents, such as bisacodyl or phenolphthalein, and mineral oil.

Figure 5A:
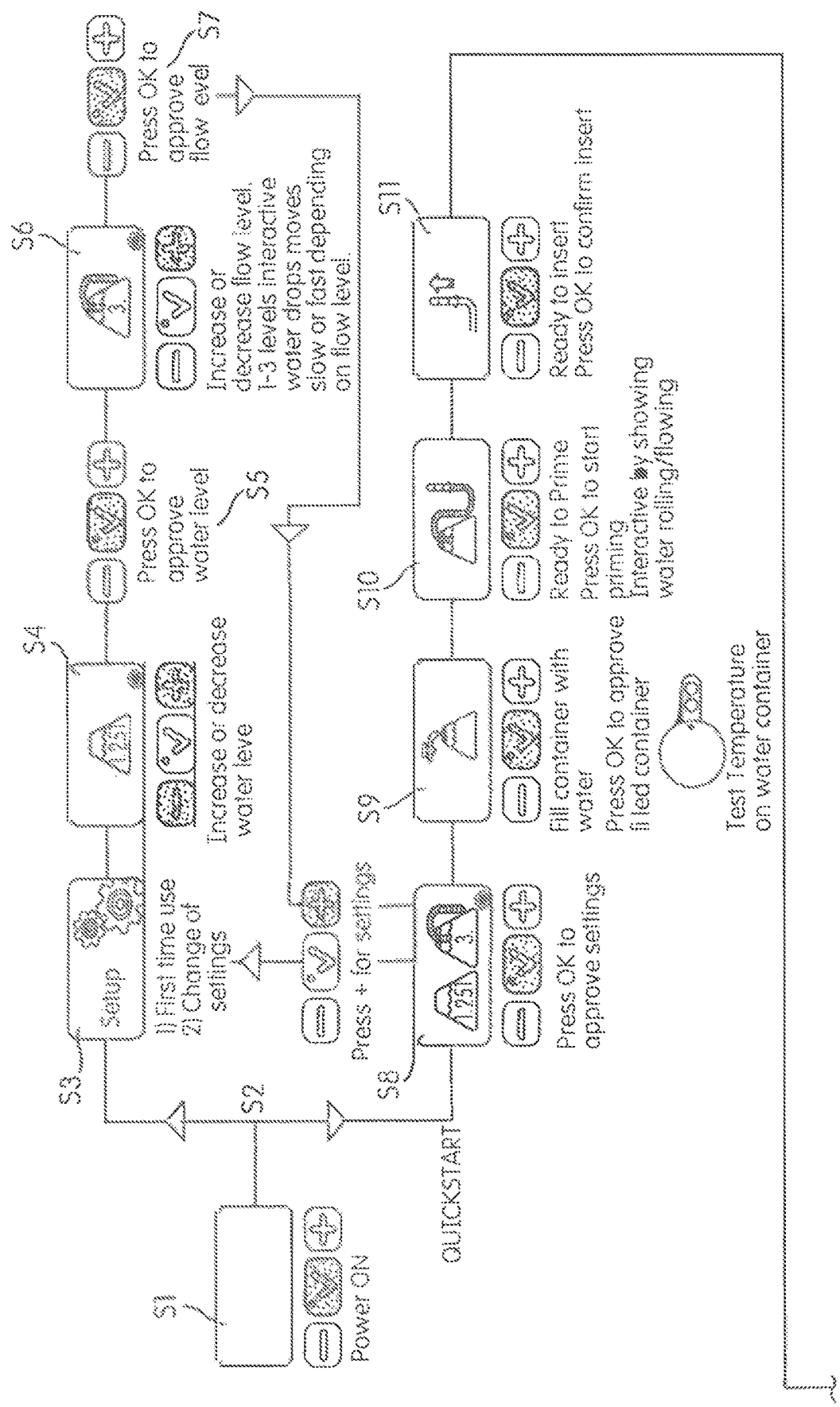
FIG. 5A is the first part of a schematic overview of the steps of an irrigation procedure using an irrigation system according to the invention.
Figure 5B:
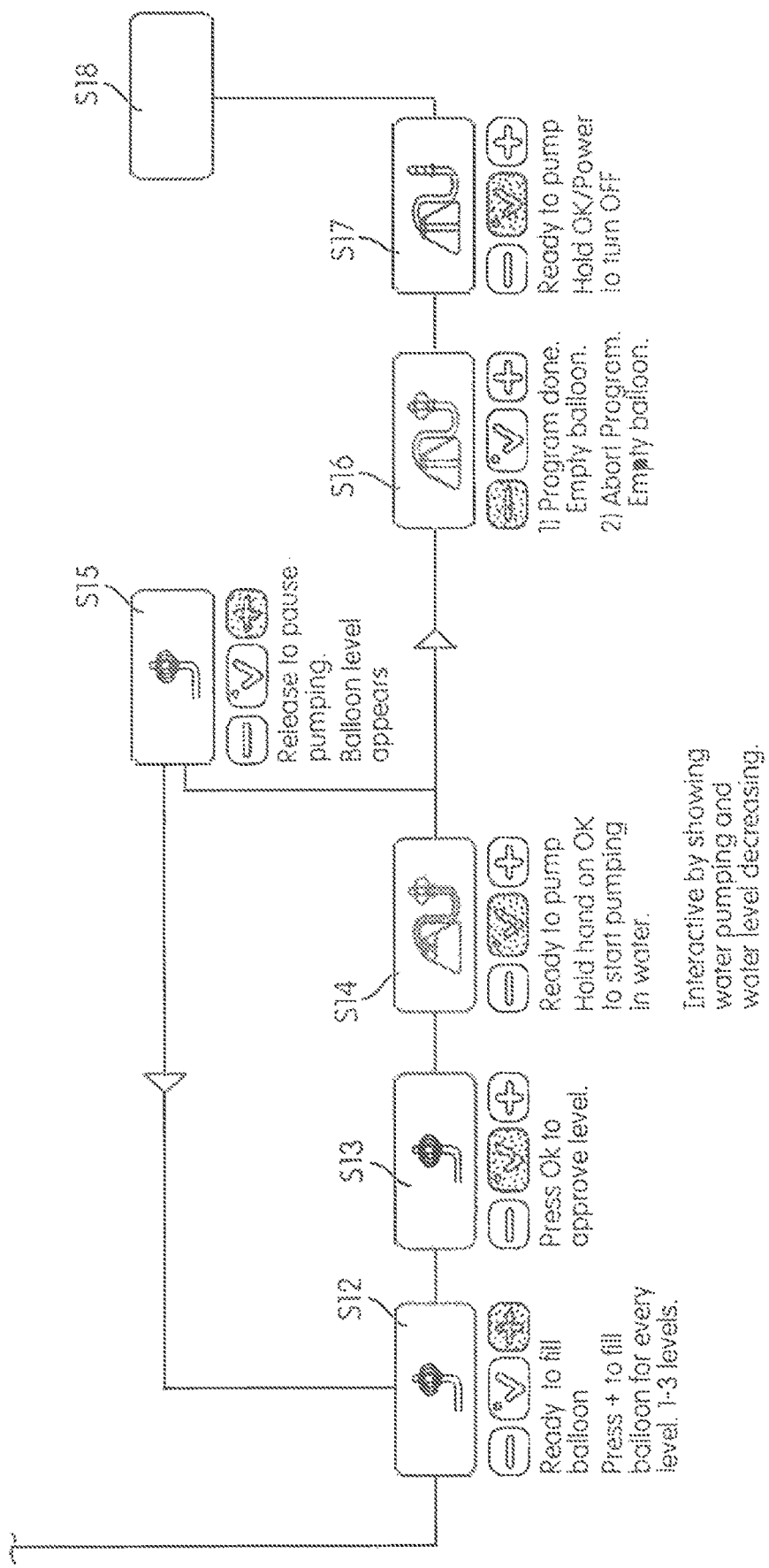
FIG. 5B is the second part of the schematic overview continuing from FIG. 5A of the steps of an irrigation procedure using an irrigation system according to the invention.

By use of the present invention, anal irrigation can be carried out by a sequence of steps, which will now be discussed with reference to the schematic illustration of possible display showings, as illustrated in FIG. 5A and FIG. 5B.

Here, three control buttons are used: one marked as "−", indicating a decrease, one marked "+", indicating an increase, and one marked "√", indicating a confirmation, OK. These buttons will be referred to in the following as "decrease", "increase" and "confirm", respectively.

In a first step S1, the control unit is activated, and a choice is made, S2, whether to enter an initiation scheme, or to quick-start the irrigation procedure. If this is the first time the irrigation system is used by the user, the initiation scheme is preferably required, whereas for a restart or a reuse of the irrigation system the quick-start path may be chosen. However, the initiation scheme may be used even after the first time, to alter the settings and the like.

In the initiation scheme, a display is first shown, S3, that a parameter setting mode is entered. In a following step, S4, the volume of irrigation liquid to be used for the irrigation is determined. The desired volume is set with the increase and decrease buttons. In a following step, S5, the set volume is accepted by pressing the confirm button. In a following step, S6, the desired flow rate is determined. Again this is done with increase and decrease. The flow rate is preferably selectable among a predetermined number of pre-selected fluid rates. For example, three different flow rate levels may be provided. In a subsequent step, S7, the selected level is confirmed.

The settings for the user are preferably stored, and are reused in the next irrigation.

The user is then asked whether the determined settings are accepted in step S8. Pressing of confirm at this stage brings the user forward to the next stage, whereas a negative confirmation, e.g. by pressing increase, brings the user back to the setting stage, step S3.

Having completed the initiation, the user is requested, in step S9, to fill up the reservoir with liquid, such as water. When this is done, confirm is pressed to confirm completion of this step. Optionally, a temperature check of the filled liquid can be done at this stage, and an alarm may be provided to the user if the temperature is too high or too low.

In a following step, S10, the user is asked to confirm that priming of the system should be made. Priming may e.g.

comprise pumping of irrigation to fill the tubing with liquid, etc. At this stage, the probe may remain in its package. If the probe is provided with a hydrophilic coating, irrigation liquid may also be pumped to ensure that the hydrophilic coating is properly wetted and activated.

When priming is completed, the user is asked, in step S11, to insert the probe in the operational position. When this has been done, this is confirmed by pressing confirm. The user is then asked to confirm that he/she is ready for filling of the balloon. Filling of the balloon is preferably made to one of a few predetermined filling levels. Here, in step S13, pressing of the increase button once fills the balloon to the first, lowest filling level. Pressing of the increase button once again fills the balloon to the second filling level. Pressing once again fills the balloon to the highest filling level. However, alternative ways of filling the balloon are feasible. For example, more or fewer predetermined filling levels may be used. Further, the filling may be performed continuously while the increase button is depressed. Further, deflation of the balloon may be obtained by pressing the decrease button. Further, the balloon may be alternatively be made by means of a separate, and preferably hand-operated, pump, as has been discussed in the foregoing. If so, the user may simply be requested to confirm that an appropriate filling level has been achieved.

In a further step, S14, the user is requested to confirm that he/she is now ready for irrigation. In this stage, continuous depression of the confirmation button is requested. The progress of the irrigation may be indicated on the display, as a progress bar, indication of volume that has been pumped or is remaining, time left, etc. If it is determined, step S15, that the confirmation button has been released prior to completion of the irrigation, the process is brought back to step S12 as a safety measure. Hereby, the activation of the pump functions as a "dead man's handle", so that irrigation will immediately be aborted if something unintentional occurs.

If the irrigation process is not aborted, the irrigation continues until the predetermined volume of irrigation liquid has been discharged. When irrigation has been completed, step S16, the user is asked to deflate the balloon by pressing decrease. When this has been done, and the probe has been removed, the user is asked to dry the system, step S17, by pressing confirm, whereby remaining irrigation liquid in the tubing is pumped out. Then, the control unit may be powered off, and the irrigation is completed, step S18.

The above-discussed irrigation process can naturally be varied in many ways, as would be apparent for the skilled addressee. For example, several of the steps may be omitted, combined or executed in a different order. For example, several of the confirmation steps may be omitted, so that the procedure can perform several of the steps automatically, without requesting confirmation from the user. The initiation/parameter setting stage may also be omitted in the default procedure, and instead being separately accessible upon request. This is e.g. of advantage in applications were parameter settings are to be made primarily by a physician or the like, and where the user is normally not intended to alter the parameter settings. However, additional steps of confirmation, parameter setting and the like may also be added to the process.

Figure 7:
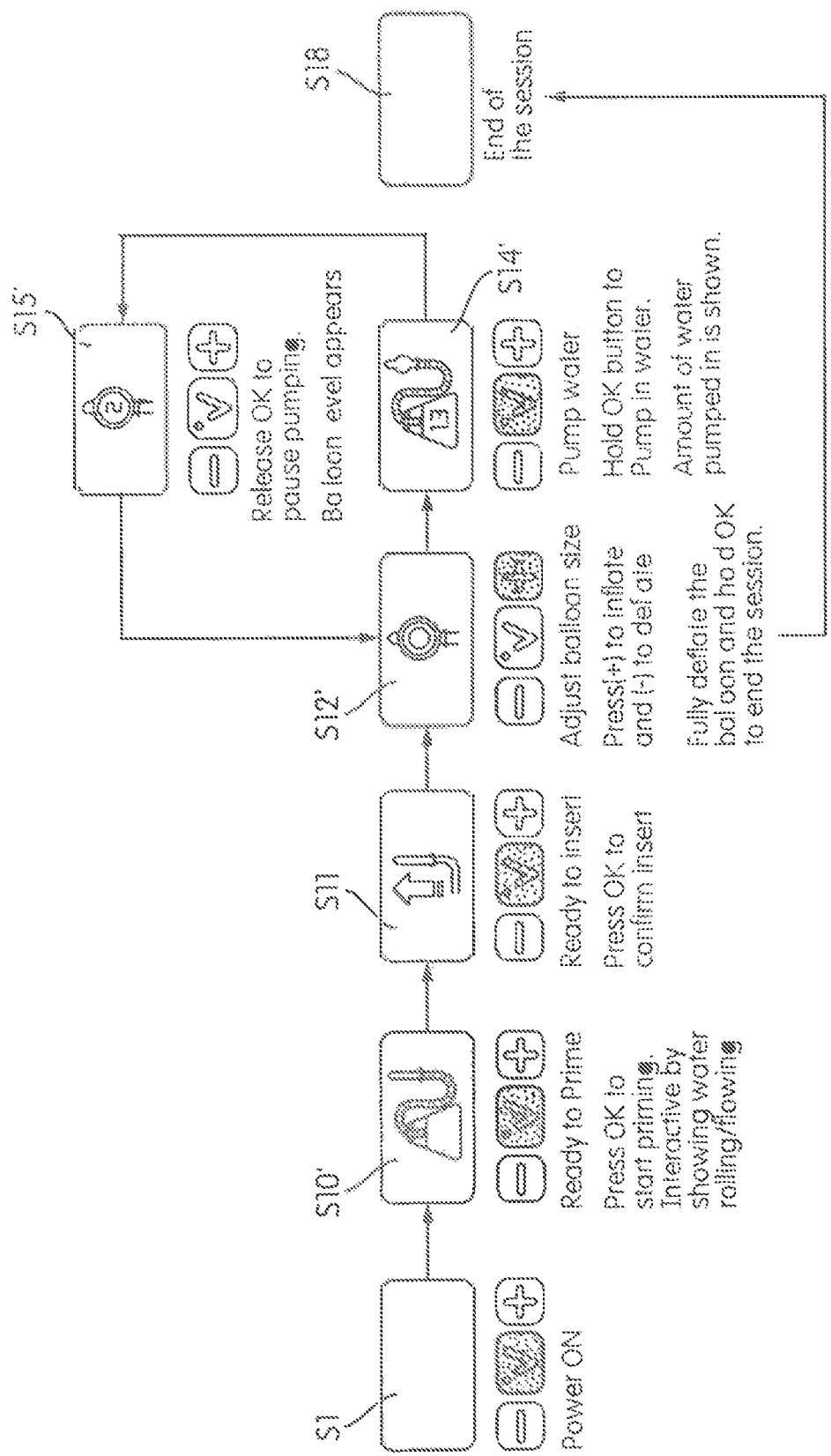
FIG. 7 is a schematic overview of the steps of an alternative embodiment of an irrigation procedure using an irrigation system according to the invention.

As a further illustration of the variations in procedural steps which are feasible, another embodiment illustrating a process involving fewer steps is will now be discussed with reference to FIG. 7. In order to simplify understanding, the same or similar steps as discussed above in relation to FIG. 5A and FIG. 5B are assigned the same or similar reference denominations.

In a first step S1, the control unit is activated.

Following activation, the process immediately proceeds to a priming step S10'. Priming may e.g. comprise pumping of irrigation to fill the tubing with liquid, etc. At this stage, the probe may remain in its package. If the probe is provided with a hydrophilic coating, irrigation liquid may also be pumped to ensure that the hydrophilic coating is properly wetted and activated.

When priming is completed, the user is asked, in step S11, to insert the probe in the operational position. When this has been done, this is confirmed by pressing confirm.

Next to follow is a balloon inflation/deflation step S12'. This step may be identical to the balloon inflation/deflation described previously in relation to FIGS. 5A and 5B. However, preferably step S12' does not operate with predetermined filling levels. Instead, the balloon is continuously inflated when the increase button is depressed. Further, filling of the balloon is preferably immediately aborted as soon as the button ceases to be depressed. Similarly, the balloon is continuously deflated when the increase button is depressed. Further, deflation of the balloon is preferably immediately aborted as soon as the button ceases to be depressed. Hereby, the user can easily inflate the balloon to a desired level by keeping the increase button depressed until a desired filling level has been obtained, and thereafter release the button. The filling level may then be fine adjusted by short term depression of the increase and decrease buttons, thereby to adjust the filling level upwards or downwards, respectively. When a satisfactory balloon filling level has been obtained, this is confirmed by activating the confirm button. This also confirms that the user is now ready for irrigation.

In this step S14', depression of the confirmation button, or alternatively the increase button, activates pumping of the irrigation liquid through the catheter. The progress of the irrigation may be indicated on the display, as a progress bar, indication of volume that has been pumped or is remaining, time left, etc. Pumping continues as long as the button continues to be depressed. However, as soon as the button is released, pumping is immediately aborted, in analogy to what has been discussed previously. Hereby, the activation of the pump functions as a "dead man's handle", so that irrigation will immediately be aborted if something unintentional occurs. Pumping may also optionally be automatically aborted, despite depression of the button, if it is determined that the reservoir holding the irrigation liquid has been emptied. Pumping may also optionally be automatically aborted, despite depression of the button, when it is determined that a predetermined irrigation volume has been irrigated.

When pumping has been stopped or aborted, the process proceeds to step S15', in which the user is informed that pumping has been aborted, and/or the level of balloon inflation is presented. Other information may also be presented to the user in this step. Further, this step may also be omitted.

After a predetermined time, or after confirmation by the user, e.g. by depressing the confirm button, or alternatively immediately after abortion of pumping of the irrigation liquid (in case step S15' is omitted), the process returns to step S12'. Here, the user may re-adjust the filling level of the balloon, as described previously, by using the increase and decrease buttons. The user may also confirm that the balloon pressure is satisfactory, and again proceed to the irrigation step S14' by depressing the confirm button. However, if it is or has been determined that the reservoir holding the irrigation liquid has been emptied and/or that a predetermined irrigation volume has been irrigated, proceeding to step S14' may optionally be hindered.

In step S12', the balloon may further be deflated for withdrawal of the catheter, after completed irrigation or when a user wishes to abort the procedure prior to completeness. Deflation is accomplished by continuous depression of the decrease button. When the balloon has been deflated, the user confirms this by depression of the confirm button, and the process then ends in step S18.

Even in the simplified procedure discussed above in relation to FIG. 7, a parameter setting mode or the like may optionally be provided, e.g. to determine a predetermined irrigation volume to be used for irrigation, to adjust the pumping speed for inflating/deflating the balloon and/or for pumping the irrigation liquid, etc. The parameter setting mode may be entered by simultaneous depression of two or more of the control buttons, by activation of a further control button, by connecting the control unit to an external device, or the like.

Additionally or alternatively, it is possible to use switches also sensing the pressure level being applied by the user, and to adapt e.g. the pumping speed in accordance with the determined pressure level. For example during the irrigation step S14 or S14', it may be determined if the applied pressure to the confirm button is exceeding a certain threshold level, and if so use a higher pumping speed, and if not, to use a lower pumping speed. More than two speeds may also be provided. Pumping may also optionally be automatically aborted, despite depression of the button, if it is determined that the reservoir holding the irrigation liquid has been emptied.

Further, the pumping speed may directly correlated to the applied pressure. As another example, it is possible, in addition or as an alternative, to adapt the pumping speed for inflation and/or deflation of the balloon in the same manner. Alternatively, the user may be given the opportunity of determining the pumping speed by provision of two or more control buttons related to "increase", "decrease" and "confirm". For example, a high speed and low speed increase button may be provided, a high speed and low speed confirm button, and/or a high speed and low speed decrease button. The user may then select whether to use the high or low speed for a certain action. When different speeds are not available or not applicable, the two or more buttons may correspond to identical function(s).

It is also possible to use other types of control units, and to implement the dead man's handle functionality in relation to other types and configurations of control elements. One such alternative embodiment of a control unit is illustrated in FIG. 8.

In the control unit of FIG. 8, the control unit 31' is provided with separate control elements, here in the form of control buttons, for irrigation and for inflation/deflation of the balloon on the probe, respectively.

It is possible to use the same control element for both inflation and deflation of the probe, e.g. by using a rocker lever or the like, having three states—inflation, deflation and non-operative. The non-operative state should be default, and as discussed above, the non-operative state should automatically be resumed as soon as the control element is released. However, preferably separate control elements, such as buttons are used for inflation and deflation, respectively. In the illustrative example, a first button 41 is used for deflation of the balloon, and a second button 42 is used for inflation of the balloon. Again, the buttons are only operative when depressed, and release of the buttons will immediately stop the inflation/deflation processes.

Similarly, the irrigation is controlled by one or several control elements. For irrigation, only one operation is normally required, viz. to activate the pump to provide irrigation fluid to be transferred to the user through the probe. This may be controlled by a control button 44, as in the illustrative example. Irrigation will, as discussed above, immediately be aborted once the button 44 is released. A further control button 43 may be provided for reverse operation, e.g. to empty the tubes and the probe from irrigation fluid once irrigation has been completed, and/or to release overpressure from the irrigation liquid reservoir. This control element is preferably also provided with a dead man's handle functionality. Alternatively, a single control element with several operation states, such as a rocker lever, may be used here as well.

The arrangement of separate control elements for controlling the balloon on the one hand, and the irrigation on the other, presents several advantages. For example, the control unit becomes simpler and less costly to produce. Further, the operation becomes more transparent and controllable for the user.

It is possible to make the control elements for the balloon and the irrigation, respectively, to be operable only one at a time, i.e. to lock the other control elements when one is used. However, preferably the control elements for the balloon and irrigation, respectively, are operable simultaneously. This makes it possible for the user to adjust the balloon filling, by inflation or deflation, during irrigation. User's often experience that a balloon filling level which is initially considered satisfactory, is considered less satisfactory when the irrigation is started, and the surrounding environments is different, or after a certain time. Simultaneous operability of the control elements makes it possible to easily adjust the balloon filling level without the need to abort the irrigation, to enter any specific balloon inflating position or state and liquid transferring position or state, and the like. The whole irrigation procedure hereby becomes easier, faster and easier to control.

The person skilled in the art realizes that the present invention is not limited to the preferred embodiment. For example many different types of hand-operated or powered pumps may be used. Further, the control elements may be realized in many different ways, such as mechanical control buttons, galvanically isolated touch buttons, areas on a touch screen and the like. The control elements may also, additionally or alternatively, be arranged on a remote control. Also, the pumping of the irrigation liquid may be direct or indirect.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A portable irrigation system, comprising:
   a reservoir for an irrigation liquid;
   a probe for arrangement in a user;
   an electrical system, comprising:
      an electrical pump to directly or indirectly pump the irrigation liquid from the reservoir to the probe;
   a control unit coupled to the electrical pump to control the electrical pump, and thereby also to transfer said irrigation liquid; and
   tubing to provide fluid communication between said reservoir, said control unit and said probe;
   wherein said control unit comprises at least one manually operable control element to control said electrical pump, said control element being switchable between an activated state, in which the electrical pump is controlled to pump irrigation liquid, and a deactivated state, in which the electrical pump is controlled not to pump irrigation liquid, and wherein the control element is brought into the activated state by continuous application of a predetermined condition thereto, and wherein the control element is immediately brought to the deactivated state when the predetermined condition ceases to be applied, thereby aborting pumping of the irrigation liquid, wherein the probe further comprises an inflatable retention member and wherein separate control elements are provided for inflation and deflation of the inflatable retention member, said control elements being operative when depressed and immediately stopping the inflation or deflation process upon release.

2. The portable irrigation system of claim 1, wherein the predetermined condition to bring the control element into the activated state is at least one of a depression, a twisting, a rotating, a pulling or a pushing.

3. The portable irrigation system of claim 1, wherein the control unit is connected to the rest of the irrigation system by means of wire.

4. The portable irrigation system of claim 1, wherein the control unit is a remote control, which is wirelessly connected to the portable irrigation system.

5. The portable irrigation system of claim 4, wherein the remote control is at least one of: a smart phone, a tablet computer or a laptop computer.

6. The portable irrigation system of claim 1, wherein the electrical pump is arranged within the control unit.

7. The portable irrigation system of claim 1, wherein the control unit is programmable.

8. The portable irrigation system of claim 7, wherein the control unit is programmable to set at least one of: a total irrigation liquid volume to be discharged or an irrigation liquid discharge flow rate.

9. The portable irrigation system of claim 1, wherein the control unit comprises at least two control elements.

10. The portable irrigation system of claim 9, wherein at least one of the control element(s) is a multi-purpose control element having different functions in different operation states.

11. The portable irrigation system of claim 1, wherein the electrical pump is useable both for pumping the irrigation liquid for discharge through the probe and for pumping a fluid for filling an inflatable retention member on the probe.

12. The portable irrigation system of claim 1, wherein the electrical pump is useable for pumping the irrigation liquid for discharge through the probe, and wherein a second pump is provided for inflation of an inflatable retention member on the probe.

13. The portable irrigation system of claim 1, wherein the control unit is arranged to transmit operation related data to a remote unit via wireless communication.

14. The portable irrigation system of claim 1, wherein the control unit further comprises a display.

15. The portable irrigation system of claim 1, wherein the reservoir comprises an overpressure release valve to release pressure over a predetermined maximum pressure.

16. The portable irrigation system of claim 1, wherein the irrigation system is a rectal irrigation system, and wherein the probe is a rectal probe.

17. The portable irrigation system of claim 1, wherein the control unit forms a unitary, hand-held unit enclosing the electrical system, including said electrical pump and the at least one manually operable control element.

18. The portable irrigation system of claim 17, wherein the control unit forming the unitary hand-held unit further comprises a display.

19. The portable irrigation system of claim 17, wherein the unitary hand-held unit is provided within a waterproof housing.

20. The portable irrigation system of claim 1, wherein the control unit is distantly arranged from both the reservoir and the probe, and connected to the reservoir and the probe, respectively, through the tubing.

21. A portable irrigation system comprising:
    a reservoir for an irrigation liquid;
    a probe for arrangement in a user;
    an electrical system, comprising:
       an electrical pump to directly or indirectly pump the irrigation liquid from the reservoir to the probe;
    a control unit to control the electrical pump, and thereby also control the transfer of said irrigation liquid; and
    tubing to provide fluid communication between said reservoir, control unit and probe;
    wherein said control unit comprises at least one manually operable control element to control said electrical pump, said control element configured as a dead man's handle, thereby immediately returning to a deactivated state, in which the electrical pump ceases to pump the irrigation liquid, when manual operation of the control element is aborted, wherein the probe further comprises an inflatable retention member and wherein separate control elements are provided for inflation and deflation of the inflatable retention member, said control elements being operative when depressed and immediately stopping the inflation or deflation process upon release.

22. The portable irrigation system of claim 21, wherein the control unit is a unitary, hand-held unit enclosing the electrical system, including said electrical pump and the at least one manually operable control element.

23. The portable irrigation system of claim 21, wherein the control unit is distantly arranged from both the reservoir and the probe, and connected to the reservoir and the probe, respectively, through the tubing.

* * * * *